United States Patent [19]
Boyce et al.

[11] Patent Number: 5,910,616
[45] Date of Patent: Jun. 8, 1999

[54] VAPOR PHASE PROCESS FOR PREPARING FLUORINATED ALIPHATIC COMPOUNDS

[75] Inventors: C. Bradford Boyce, Baton Rouge; Randolph K. Belter, Zachary, both of La.

[73] Assignee: LaRoche Industries, Inc., Atlanta, Ga.

[21] Appl. No.: 09/100,997

[22] Filed: Jun. 22, 1998

[51] Int. Cl.$^6$ .................................................. C07C 17/08
[52] U.S. Cl. ............................................................ 570/167
[58] Field of Search .............................................. 570/167

[56] References Cited

U.S. PATENT DOCUMENTS

| | | | |
|---|---|---|---|
| 5,091,602 | 2/1992 | Park et al. | 570/167 |
| 5,202,509 | 4/1993 | Laviron et al. | 570/167 |

*Primary Examiner*—Alan Siegel
*Attorney, Agent, or Firm*—Richard J. Hammond

[57] ABSTRACT

A process is disclosed for the preparation of a fluorinated aliphatic hydrocarbon. The process utilizes a $C_1$ to $C_6$ hydrocarbon substituted with a halogen selected from the group consisting of chlorine, bromine and iodine as the starting material. The alkyl hydrocarbon is reacted in the vapor phase at a temperature from about 75° to about 150° C. with hydrogen fluoride and a catalytically effective amount of at least one antimony compound having the formula $$Sb_w{}^uM_x{}^vX_yF_z \cdot nHF$$

where n is 0 or an integer that is at least 1; M is selected from the group consisting of a metal from Group IIIa, IIIb, IVa, IVb, Va, Vb, VIa, VIb, VIIb and VIII of the Periodic Table of the Elements; X is chloro, bromo or iodo; u is an integer that is the valence of antimony; v is an integer that is the valence of M; w, x and z are an integer of at least 1; y is 0 or an integer of at least 1; and $(w \cdot u)+(x \cdot v)=y+z$ said at least one antimony compound being a nonvolatile solid at the temperature of the reaction, for a time sufficient to form said fluorinated aliphatic hydrocarbon.

In order to conduct the process of the present invention, the antimony compound must be a nonvolatile solid at the temperature of the reaction. The reaction is carried out for a time sufficient to form said fluorinated aliphatic hydrocarbon.

The fluorinated aliphatic hydrocarbon is subsequently separated from the vapor phase reactants and recovered.

The process is particularly suitable for the preparation of 1,1,1,3,3-pentafluoropropane.

10 Claims, No Drawings

VAPOR PHASE PROCESS FOR PREPARING FLUORINATED ALIPHATIC COMPOUNDS

FIELD OF INVENTION

This invention relates to a process for preparing aliphatic compounds substituted with multiple fluorine atoms. In particular, this invention relates to the discovery that a highly fluorinated aliphatic hydrocarbon can be prepared in high yield by a process comprising treating a chlorofluoro olefin with hydrogen fluoride in the vapor phase in the presence of a catalyst that is a metal oxide, metal halide or mixture thereof for a time sufficient to form said highly fluorinated aliphatic hydrocarbon.

BACKGROUND OF THE INVENTION

Chlorofluorocarbons (CFC's) are widely used in refrigerant compositions, propellants and cooling fluids as well as blowing agents, solvents and rinse agents. Their replacement with environmentally acceptable alternatives has produced an abundance of compounds meeting one or more of these needs. The most acceptable replacement compounds are those having little or no chlorine, since it is generally accepted that chlorinated aliphatics lead to unacceptable reactive chlorine-containing radicals when present in the upper atmosphere. These radicals are thought to react with the ozone in the stratosphere depleting it to dangerously low levels.

One of the more promising alternatives to CFC's are aliphatic compounds where chlorine has been replaced with fluorine. These materials are known as hydrofluorocarbons (HFC's). Typical HFC's have atmospheric lifetimes and global warming potentials that are a fraction of their chlorinated analogs. Fortunately, many of their other physical properties (low flammability and toxicity, sufficient volatility, etc.) are identical or similar to the CFC's. Accordingly, they are attractive replacements for the chlorinated molecules.

In processes for preparing HFC's, a usual starting material is the chlorinated analog of the desired fully fluorinated compound. Thus, U.S. Pat. No. 2,787,646 discloses that $SbF_3Cl_2$ and\or $SbF_3$ are useful for converting compounds of the formula $CMZ_2CX=CHY$, for example 3,3,3-trichloroprop-1-ene or 1,1,3-trichloroprop-1-ene to compounds of the formula $CF_3CX=CHY$, for example 3,3,3-trifluoroprop-1-ene.

U.S. Pat. No. 2,549,580 discloses the conversion of 1,1-dichloroprop-1-ene to 1,1,1-trifluoropropane by means of HF at 120° C. and 800 psi pressure.

U.S. Pat. No. 5,616,819 discloses a two step process for the preparation of fully fluorinated aliphatic hydrocarbons in which hydrogen fluoride is reacted with a chlorofluoro olefin in the presence of a catalyst for a time and at a temperature sufficient to form said fully fluorinated aliphatic hydrocarbon.

The preparation of 1-chloro-1,1,3,3,3-pentafluoropropane and of 1,1,1,3,3,3-hexafluoropropane from 1,1,1,3,3,3-hexachloropropane in the liquid phase is described in EPO Publication No. 0 522 639 A1. While the preferred catalyst for the reaction is noted to be $SbCl_5$, other catalysts disclosed are those metal chlorides, fluorides, and chloride fluorides of Group IIIa, IVa, IVb, Va, Vb and VIb of The Periodic Table of the Elements.

Compounds such as 1,1,1,3,3,3-hexafluoropropane are prepared by the coupling of two chlorine containing reactants, i.e., 1,1,1-trichloro-2,2,2-trifluoroethane and dichlorodifluoromethane, in the presence of hydrogen and a first catalyst to form an olefin, i.e., 1,1,1,3,3-pentafluoro-2-chloroprop-2-ene and then hydrogenating the olefin in the presence of a second catalyst. See WO 95/05353.

SUMMARY

The process of the present invention for preparing a fluorinated aliphatic hydrocarbon utilizes a $C_1$ to $C_6$ hydrocarbon substituted with a halogen selected from the group consisting of chlorine, bromine and iodine as the starting material. The $C_1$ to $C_6$ hydrocarbon is reacted in the vapor phase at a temperature from about 75° to about 150° C. with hydrogen fluoride and a catalytically effective amount of at least one antimony compound having the formula

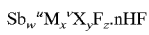

where n is 0 or an integer that is at least 1; M is selected from the group consisting of a metal from Group IIIa, IIIb, IVa, IVb, Va, Vb, VIa, VIb, VIIb and VIII of the Periodic Table of the Elements; X is chloro, bromo or iodo; u is an integer that is the valence of antimony; v is an integer that is the valence of M; w, x and z are an integer of at least 1; y is 0 or an integer of at least 1; and (w·u)+(x·v)=y+z said at least one antimony compound being a nonvolatile solid at the temperature of the reaction.

In order to conduct the process of the present invention, the antimony compound must be a nonvolatile solid at the temperature of the reaction. The reaction is carried out for a time sufficient to form said fluorinated aliphatic hydrocarbon.

The fluorinated aliphatic hydrocarbon is subsequently separated from the vapor phase reactants and recovered.

DESCRIPTION OF THE PREFERRED EMBODIMENTS

The process of the present invention is particularly useful for producing highly fluorinated aliphatic compounds that are not easily prepared in typical fluorine for chlorine substitution reactions.

Thus, for example, in the catalyzed reaction of 1,1,1,3,3-pentachloropropane with hydrogen fluoride, fluorine substitution for chlorine is accompanied by large amounts of tar and byproducts. As a result, the desired pentafluoro compound is not formed in commercially acceptable yields.

Similarly, polychloro olefins such as 1,1,3,3-tetrachloroprop-1-ene with anhydrous hydrogen fluoride and a typical catalyst fail to yield the desired pentafluoropropane in acceptable yield due to extensive telomerization.

The process of the present invention overcomes these disadvantages by using as the starting material, a $C_1$ to $C_6$ hydrocarbon substituted with a halogen selected from the group consisting of chlorine, bromine and iodine. Such hydrocarbons include the halo-substituted (chlorine, bromine and or iodine) optionally fluorinated ethanes, ethylenes, propanes, propylenes, butanes, butylenes and the like.

Such $C_1$ to $C_6$ hydrocarbons preferably include the chlorinated, optionally fluorinated hydrocarbons such as chlorine-substituted hydrocarbons of the formula

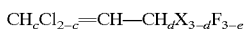

wherein X is chlorine, bromine or iodine, c is 0 or the integer 1 and d and e are 0 or the integer 1, 2 or 3 and d+e=3. The $C_1$ to $C_6$ hydrocarbons also preferably include the chlorinated, optionally fluorinated hydrocarbons such as the chlorine-substituted hydrocarbons of the formula $$CH_cCl_{3-c}—CH_2—CH_dX_{3-d}F_{3-e}$$

wherein X is chlorine, bromine or iodine, c is 0 or the integer 1 and d and e are 0 or the integer 1, 2 or 3 and d+e=3.

In the process of the present invention, at least one mole of hydrogen fluoride is required to produce the fluorinated aliphatic hydrocarbon. However, an excess of hydrogen fluoride, preferably from about 2 to about 10 times the stoichiometric requirements are typically used in this reaction to facilitate the formation of such fluorinated aliphatic hydrocarbon.

As noted, the reaction according to the process of the present invention is carried out in the vapor phase. It is preferable to conduct the process in a continuous mode. As such, the process may be carried out over a catalytic bed that is fluidized or is static. Whether fluidized- or static bed-type reactions are employed, it is preferred as noted above, that the catalyst is present in the reaction vessel prior to the introduction of the chlorofluoro olefin and hydrogen fluoride.

As pointed out previously, a variety of catalysts are useful in carrying out the reaction of these alkyl hydrocarbons and hydrogen fluoride in the vapor phase. To a large extent, many of these catalysts are equivalent and the choice of which one depends on cost and availability.

The catalysts of use in the present invention are antimony compounds having the formula $$Sb_w{}^uM_x{}^vX_yF_z \cdot nHF$$

where n is 0 or an integer that is at least 1; M is selected from the group consisting of a metal from Group IIIa, IIIb, IVa, IVb, Va, Vb, VIa, VIb, VIIb and VIII of the Periodic Table of the Elements, X is chloro, bromo or iodo, u is an integer that is the valence of antimony, v is an integer that is the valence of M, w, x and z are an integer of at least 1, y is 0 or an integer of at least 1 and (w·u)+(x·v)=y+z said at least one antimony compound being a nonvolatile solid at the temperature of the reaction.

Preferably, w is an integer from 1 to 6, x is an integer from 1 to 5 and X is chloro. These catalysts are identified herein, for convenience, as metal antimonates, e.g., aluminum antimonate, chromium antimonate and the like.

To be effective in the process of the present invention, these antimony compounds must nonvolatile solids at the temperature of the reaction, i.e., from about 75° C. to about 150° C.

Further, it should be noted that the amount of hydrogen fluoride bound to the antimonate may be 0 or it can be an amount that is more then 0, i.e., the integer 1. However, very high amounts of hydrogen fluoride (as represented by "n") will disadvantageously result in a liquid antimonate and the solid catalysts of this invention.

As disclosed above, in the antimony catalysts of the present invention, the metal "M" is selected from the group consisting of a metal from Group IIIa, IIIb, IVa, IVb, Va, Vb, VIa, VIb, VIIb and VIII of the Periodic Table of the Elements. Preferably such metal is antimony, i.e., it may be a catalyst where antimony is present as $Sb^{+5}$ and also (for M) as $Sb^{+3}$, bismuth, chromium, tin, or is selected from the group of metals in Group IVb, Vb, VIa, VIb, VIIb and VIII of the Periodic Table of the Elements.

M is preferably selected from the group consisting of aluminum, chromium, titanium, tungsten, and cobalt.

Particularly preferred antimony compounds of use in the present invention are those selected from the group consisting of the complexes having nHF associated with them of the formula: $Sb_3AlX_yF_z$; $Sb_3CrX_yF_z$; $Sb_4TiX_yF_z$; $Sb_6WX_yF_z$; and $Sb_3CoX_yF_z$ where n, X, y and z are as previously defined.

Especially preferred solid catalysts in accordance with the present invention are those where M is antimony, X is chloro and u is 5, v and w are 3, x is 1 and the sum y+Z is 18.

Specific illustrations of the catalysts of use in the present invention and their volatilization temperatures are shown below in the Table

TABLE

| Metal Composition of Antimonate Catalyst (mol/mol) | Volatilization Temp. (° C.) |
|---|---|
| $Sb_3{}^5/Cr^3$ | 246 |
| $Sb_3{}^5/Al^3$ | 240 |
| $Sb_4{}^5/Ti^4$ | 274 |
| $Sb_6{}^5/W^6$ | 256 |
| $Sb_9{}^5/W^6$ | 145 |
| $Sb_5{}^5/Ta^5$ | 345 |
| $Sb_4{}^5/Nb^5$ | 310 |

Note:
all of the above catalysts are compositions of the formula $Sb_w{}^uM_x{}^vX_yF_z \cdot nHF$, where n is >1, M, w, x, v and u are as shown in the Table, X is chloro, y and z are at least 1 and the sum of y and z is equal to the sum of (w · u) and (x · v). For example, in the compound $Sb_3{}^5/Al^3$, w = 3, u = 5, x = 1, v = 3, y is 4 and z is 14.
Volatilization temperatures were determined by TGA (Perkin Elmer Model #TGA 7).

These antimony compounds (or "antimonates") are also useful when supported on alumina, chromia, or carbon.

The process of the present invention is particularly useful for preparing 1,1,1,3,3-pentafluoropropane which comprises reacting in the vapor phase a chlorofluoro olefin of the formula $$CHCl=CH—CF_3$$

with hydrogen fluoride and a catalytically effective amount of a material selected from the group consisting of $Sb_3AlX_yF_z \cdot nHF$, $Sb_3CrX_yF_z \cdot nHF$, $Sb_4TiX_yF_z \cdot nHF$, $Sb_6WX_yF_z \cdot nHF$ and $Sb_3CoX_yF_z \cdot nHF$ where n, X, y and z are as previously defined for a time sufficient to form said 1,1,1,3,3-pentafluoropropane.

The process of the present invention is conducted in the vapor phase for a time sufficient to form the desired fluorinated aliphatic hydrocarbon. By suitable adjustment of pressure, times and temperatures for the process of the present invention typically are in the range of from about 50° C. to about 150° C. for about 1 second to about 25 seconds. Preferably the reaction temperature is from about 75° C. to about 125° C., most preferably 100° C. to about 110° C. Especially preferred reaction conditions are those at a temperature of about 100° C. for from about 1 to about 2 seconds at a pressure of from about 0 to 100 psig. It should be noted that these catalysts are surprisingly effective at temperatures that are substantially below those temperatures and pressures that are typical for prior art catalysts such as those containing chromium or aluminum, e.g., 250° to 350° C. and pressures in excess of 100 psig.

In the following examples, specific embodiments of the process of the present invention are disclosed. These are not included as limitations on the process but are for the purposes of illustration only. Temperatures are degrees Centigrade.

EXAMPLES

Example 1
Preparation of Catalyst (comparative)

The catalyst bed is activated according to one of a number of methods already disclosed in the prior art. For example see WO 95/32935. In one of the embodiments of the process illustrated herein, a tubular reactor, constructed of hastelloy, Nickel, Monel etc. (materials that can stand the rigors of the reaction components and conditions), is charged with ⅛" pellets of chromia. The filled tube is heated in a suitable furnace to a temperature sufficient for fluorination of the chromia to occur, e.g., 200–400° C. Anhydrous hydrofluoric acid is then allowed to flow thru the bed until adequate fluorination has occurred, typically from about 8 to about 24 hours. At this point the catalyst may be cooled and stored for future use. It may, however, be used immediately.

In anticipation of starting the feed of chlorofluoro olefin, a back pressure is allowed to build-up. Upon initiation of the feed, the back pressure controller is adjusted to compensate for generation of byproduct hydrogen chloride from the reaction.

Example 2
Preparation of 1,1,1,3,3-pentafluoropropane from 1-chloro-3,3,3-trifluoro-1-propene (comparative)

A 24 inch×1 inch diameter carbon steel reactor was charged with fluorinated chromia having a surface area of 50–75 square meters/gram and heated in a tube furnace to 350° C. An anhydrous hydrogen fluoride feed stream was initiated at 100 grams per hour (2 mole per hour). A feed of 1-chloro-3,3,3-trifluoro-1-propene was then initiated at 65 grams per hour (0.5 mole per hour). The pressure of the system was maintained at 200 psig and the outflow stream collected over ice. The yield of 1,1,1,3,3-pentafluoropropane was 80% (by gas chromatograph).

Example 3
Preparation of 1,1,1,3,3-pentafluoropropane from 1-chloro-3,3,3-trifluoro-1-propene (comparative)

A 24 inch×1 inch diameter carbon steel reactor was charged with fluorinated chromia having a surface area of 102–105 square meters per gram and heated in a tube furnace to 250° C. An anhydrous hydrogen fluoride feed stream was initiated at 100 grams per hour (2 mole per hour). A feed of 1-chloro-3,3,3-trifluoro-1-propene was then initiated at 65 grams per hour (0.5 mole per hour). The pressure of the system was maintained at 200 psig and the outflow stream collected over ice. No reaction was observed.

The temperature of the reactor was raised from 250° to 350° C. using the same reactants and conditions shown above for this Example. The effluent became brown. No product phase was observed.

The Example was repeated with a fresh charge of catalyst and a temperature of 350° C. Initially, a product stream of 1,1,1,3,3-pentafluoropropane was recovered in 49% yield. However, after two hours of operation, the product stream turned to a brown color and the production of the product, 1,1,1,3,3-pentafluoropropane ceased.

Example 4
Preparation of 1,1,1,3,3-pentafluoropropane from 1-chloro-3,3,3-trifluoropropene Antimony pentachloride (260 grams) and 39 grams of aluminum chloride were charged into an autoclave. Hydrofluoric acid (1100 grams) was added with stirring. The autoclave was then heated to 100° C. for one hour. The excess hydrofluoric acid was allowed to vent and the solid antimony/aluminum halide residue was pelletized. A 24 inch×1 inch diameter carbon steel reactor was charged with the pelletized catalyst. The reactor was heated to 150° C. and an anhydrous hydrofluoric acid stream added at 100 grams per hour (5.0 mol/hr). A feed of 1-chloro-3,3,3-trifluoropropene was then initiated at 65 grams per hour (0.5 mol/hr). The pressure of the system was maintained at 50 psig and the outflow stream collected on ice. The yield if 1,1,1,3,3-pentafluoropropane was 40% (by gas chromatograph).

Example 5
Preparation of 1,1,1,3,3-pentafluoropropane from 1-chloro-3,3,3-trifluoropropene Activated carbon (100 grams) was wetted with a mixture of 98 grams of antimony pentachloride and 15.6 grams of titanium tetrachloride. A 12 inch×1 inch diameter carbon steel reactor was charged with the mixed metal halide-supported carbon. The reactor was heated to 50° C. and an anhydrous hydrofluoric acid feed was initiated slowly. Over a period of several hours, the temperature was increased to 200° C. and the feed of hydrofluoric acid adjusted to 100 grams per hour (2.0 mol/hr). A feed of 1-chloro-3,3,3-trifluoropropene was then initiated at 65 grams per hour (0.5 mol/hr). The pressure of the system was maintained at 100 psig and the outflow stream collected on ice. The yield if 1,1,1,3,3-pentafluoropropane was 43% (by gas chromatograph).

Example 6
Preparation of 1,1,1,3,3-pentafluoropropane from 1-chloro-3,3,3-trifluoropropene Chromia pellets (365 grams) were fluorinated as described in Example 1. The cooled pellets were then wetted with 108 grams of antimony pentachloride. A 24 inch×1 inch diameter carbon steel reactor was charged with the antimony pentachloride/fluorinated chromia. The reactor was heated to 50° C. and an anhydrous hydrofluoric acid feed was initiated slowly. Over a period of several hours, the temperature was increased to 150° C. and the feed of hydrofluoric acid adjusted to 100 grams per hour (5.0 mol/hr). A feed of 1-chloro-3,3,3-trifluoropropene was then initiated at 65 grams per hour (0.5 mol/hr). The pressure of the system was maintained at 50 psig and the outflow stream collected on ice. The yield if 1,1,1,3,3-pentafluoropropane was 80% (by gas chromatograph).

Example 7
Preparation of Antimony/Aluminum Chlorofluoride

Into an autoclave were charged 26.0 g of antimony pentachloride and 3.9 g of aluminum chloride. A charge of 110 g of hydrogen fluoride was added with stirring into the autoclave and the resulting mixture heated to 100° C. for 1 hour. The excess was then allowed to vent. The mixture in the autoclave was subjected to vacuum pressure (using a water aspirator) to remove any residual hydrogen fluoride. The antimony, aluminum salt was isolated from the reactors as a yellow powder.

Example 8
Preparation of Antimony/Chromium Chlorofluoride

Into an autoclave were charged 29.9 g of antimony pentachloride and 5.2 g of chromium (III) chloride. A charge of 45 g of hydrogen fluoride was added with stirring into the autoclave and the resulting mixture heated to 170° C. for 16 hour. The excess was then allowed to vent. The mixture in the autoclave was subjected to vacuum pressure (using a water aspirator) to remove any residual hydrogen fluoride.

7

The antimony, chromium salt was isolated from the reactor as a grey powder.

Example 9
Preparation of Antimony/Tungsten Chlorofluoride

Into an autoclave were charged 71.8 g of antimony pentachloride and 15.8 g of tungsten (VI) chloride. A charge of 45 g of hydrogen fluoride was added with stirring into the autoclave and the resulting mixture heated to 100° C. for 1 hour. The excess was then allowed to vent. The mixture in the autoclave was subjected to vacuum pressure (using a water aspirator) to remove any residual hydrogen fluoride. The antimony, tungsten salt was isolated from the reactor as a white powder

Example 10
Preparation of Antimony/Titanium Chlorofluoride

Into an autoclave were charged 45.0 g of antimony pentachloride and 7.0 g of titanium (IV) chloride. A charge of 24 g of hydrogen fluoride was added with stirring into the autoclave and the resulting mixture heated to 80° C. for 1 hour. The excess was then allowed to vent. The mixture in the autoclave was subjected to vacuum pressure (using a water aspirator) to remove any residual hydrogen fluoride. The antimony, titanium salt was isolated from the reactor as a white powder.

Example 11
Preparation of Antimony/Tantalum Chlorofluoride

Into an autoclave were charged 74.8 g of antimony pentachloride and 17.9 g of tantalum (V) chloride. A charge of 45 g of hydrogen fluoride was added with stirring into the autoclave and the resulting mixture heated to 100° C. for 1 hour. The excess was then allowed to vent. The mixture in the autoclave was subjected to vacuum pressure (using a water aspirator) to remove any residual hydrogen fluoride. The antimony\tungsten salt was isolated from the reactor as a white powder.

Example 12
Preparation of Antimony/Niobium Chlorofluoride

Into an autoclave were charged 74.8 g of antimony pentachloride and 13.5 g of niobium (V) chloride. A charge of 45 g of hydrogen fluoride was added with stirring into the autoclave and the resulting mixture heated to 80° C. for 1 hour. The excess was then allowed to vent. The mixture in the autoclave was subjected to vacuum pressure (using a water aspirator) to remove any residual hydrogen fluoride. The antimony\niobium salt was isolated from the reactor as a white powder.

We claim:

1. A process for preparing a fluorinated aliphatic hydrocarbon said process comprising reacting a $C_1$ to $C_6$ hydrocarbon substituted with at least one halo selected from the group consisting of chloro, bromo and iodo in the vapor phase at a temperature from about 75° to about 150° C. with hydrogen fluoride and a catalytically effective amount of at least one antimony compound having the formula $$Sb_w{}^uM_x{}^vX_yF_z\cdot nHF$$

where n is 0 or an integer that is at least 1; M is selected from the group consisting of a metal from Group IIIa, IIIb, IVa, IVb, Va, Vb, VIa, VIb, VIIb and VIII of the Periodic Table of the Elements; X is chloro, bromo or iodo; u is an integer that is the valence of antimony; v is an integer that is the valence of M; w, x and z are an integer of at least 1; y is 0 or an integer of at least 1; and (w·u)+(x·v)=y+z said at least one antimony compound being a nonvolatile solid at the temperature of the reaction, for a time sufficient to form said fluorinated aliphatic hydrocarbon.

2. The process according to claim 1 wherein said temperature of is from about 100° C. to about 125° C.

3. The process according to claim 1 wherein the metal in said M is selected from the group consisting of a metal from Group IIIa, IIIb, IVa, IVb, Va, Vb, VIa, VIb, VIIb and VIII of the Periodic Table of the Elements.

4. The process according to claim 3 wherein M is antimony, bismuth, chromium, tin, or is selected from the group of metals in Group IVb, Vb, VIa, VIb, VIIb and VIII of the Periodic Table of the Elements.

5. The process according to claim 4 wherein said antimony compound is supported on alumina, chromia, or carbon.

6. The process according to claim 1 wherein M is selected from the group consisting of aluminum, chromium, titanium, tungsten, and cobalt.

7. The process according to claim 6 wherein the antimony compound is complexed with nHF and is selected from the group consisting of $Sb_3AlX_yF_z$, $Sb_3CrX_yF_z$, $Sb_4TiX_yF_z$, $Sb_6WX_yF_z$ and $Sb_3CoX_yF_z$ where n is as previously defined.

8. The process according to claim 6 wherein said M is antimony, X is chloro and u is 5, v and w are 3, x is 1, y+Z is 18.

9. A process for preparing 1,1,1,3,3-pentafluoropropane which comprises reacting in the vapor phase a chlorofluoro olefin of the formula $$CHCl{=}CH{-}CF_3$$

with hydrogen fluoride and a catalytically effective amount of a material selected from the group consisting of $Sb_3AlX_yF_z\cdot nHF$, $Sb_3CrX_yF_z\cdot nHF$, $Sb_4TiX_yF_z\cdot nHF$, $Sb_6WX_yF_z\cdot nHF$ and $Sb_3CoX_yF_z\cdot nHF$ where n is 0 or an integer that is at least 1, X is chloro, bromo or iodo, and z is at least 1 for a time sufficient to form said 1,1,1,3,3-pentafluoropropane.

10. The process according to claim 9 wherein said catalyst is aluminum antimonate on alumina or chromium antimonate on chromia.

* * * * *